US00PP35843P2

(12) United States Plant Patent
Masor

(10) Patent No.: US PP35,843 P2
(45) Date of Patent: May 28, 2024

(54) ***ANGELONIA* PLANT NAMED 'BALANGFLRAN'**

(50) Latin Name: *Angelonia angustifolia*
Varietal Denomination: Balangflran

(71) Applicant: Ball Horticultural Company, West Chicago, IL (US)

(72) Inventor: Laura L. Masor, Buda, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/516,266

(22) Filed: Nov. 21, 2023

(51) Int. Cl.
*A01H 5/02* (2018.01)
*A01H 6/00* (2018.01)

(52) U.S. Cl.
USPC ..... Plt./404

(58) Field of Classification Search
USPC ..... Plt./404
CPC ..... A01H 5/02; A01H 5/00; A01H 6/00
See application file for complete search history.

(56) References Cited

U.S. PATENT DOCUMENTS

PP28,459 P2 * 9/2017 Nguyen ..... A01H 5/02
Plt./404

* cited by examiner

*Primary Examiner* — June Hwu
(74) *Attorney, Agent, or Firm* — Audrey Charles

(57) ABSTRACT

A new and distinct cultivar of *Angelonia* plant named 'Balangflran', characterized by its dark purplish-red colored flowers, dark green-colored foliage, and vigorous, semi-upright growth habit, is disclosed.

1 Drawing Sheet

Latin name of genus and species of plant claimed: *Angelonia angustifolia.*

Variety denomination: 'Balangflran'.

BACKGROUND OF THE INVENTION

The present invention relates to a new and distinct cultivar of *Angelonia* plant botanically known as *Angelonia angustifolia* and hereinafter referred to by the cultivar name 'Balangflran'.

The new cultivar originated in a controlled breeding program in Guadelupe, California during July 2018. The objective of the breeding program was the development of *Angelonia* cultivars having vibrant and novel flower colors and a semi-upright growth habit.

The new *Angelonia* cultivar is the result of cross-pollination. The female (seed) parent of the proprietary *Angelonia angustifolia* breeding selection coded ANG-07360-01, not patented, characterized by its dark pink-colored flowers, dark green-colored foliage, and moderately vigorous, spreading growth habit. The male (pollen) parent of the new cultivar is the proprietary *Angelonia angustifolia* breeding selection coded ANG-07321-01, not patented, characterized by its dark red-colored flowers, dark green-colored foliage, and moderately vigorous, upright growth habit. The new cultivar was selected as a single flowering plant within the progeny of the above stated cross-pollination during May 2019 in a controlled environment in Guadelupe, California.

Asexual reproduction of the new cultivar by terminal stem cuttings since May 2019 in Guadelupe, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balangflran' as a new and distinct cultivar of *Angelonia* plant:

1. Dark purplish-red colored flowers;
2. Dark green-colored foliage; and
3. Vigorous, semi-upright growth habit.

Plants of the new cultivar differ from plants of the female parent primarily in having a more upright growth habit and redder-colored flowers. Plants of the new cultivar differ from plants of the male parent primarily in having a more spreading growth habit and more purple-colored flowers.

Of the many commercially available *Angelonia* cultivars, the most similar in comparison to the new cultivar is Archangel Cherry 'Balarcher', U.S. Plant Pat. No. 28,459. However, in side-by-side comparison, plants of the new cultivar differ from plants of 'Balarcher' in at least the following characteristics:

1. Plants of the new cultivar have a darker purplish-red color than plants of 'Balarchar'; and
2. Plants of the new cultivar have a more spreading growth habit than plants of 'Balarchar'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balangflran'. The approximately 4-month-old plants were grown in 3-gallon containers for approximately 9 weeks in an outdoor nursery in West Chicago, Ill. Treatments are described below in the Detailed Botanical Description.

DETAILED BOTANICAL DESCRIPTION

Figure 1:
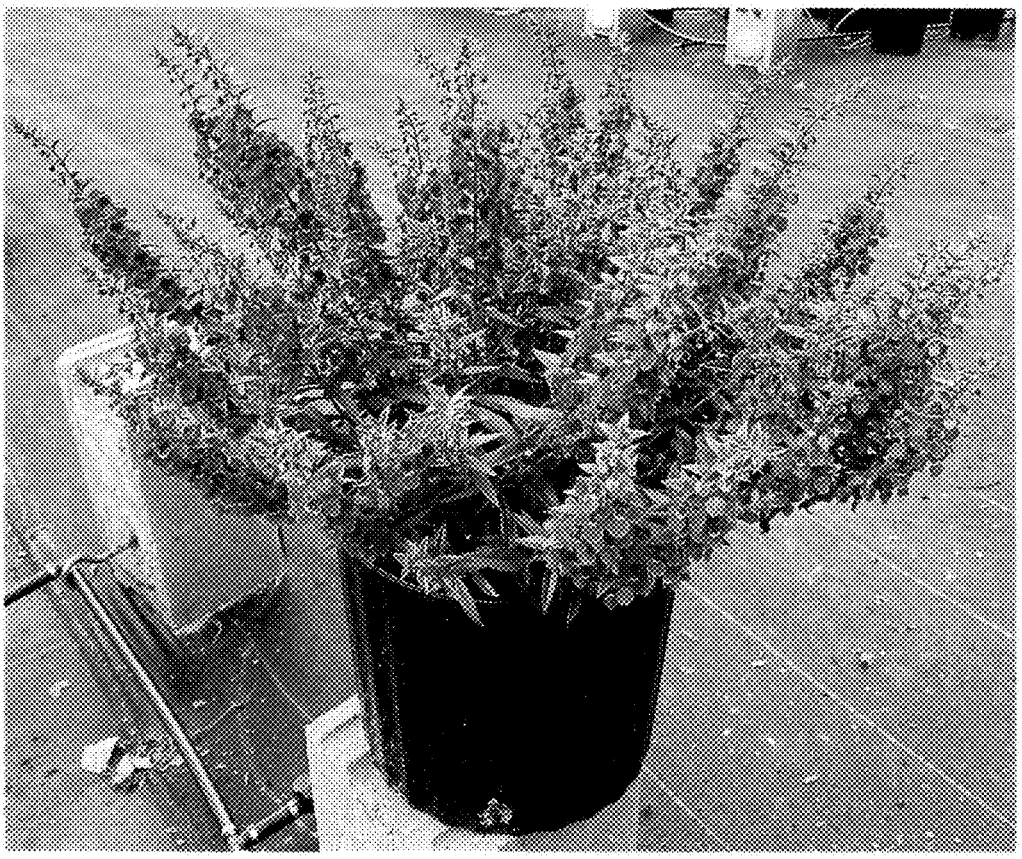
FIG. 1 illustrates a side view of the overall growth and flowering habit of 'Balangflran'.
Figure 2:
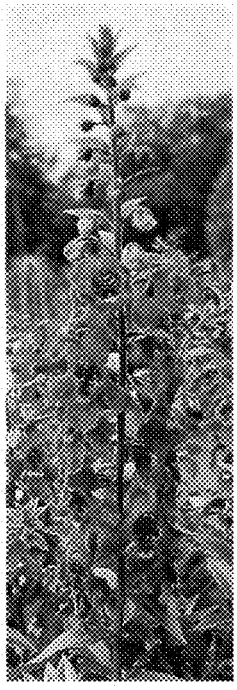
FIG. 2 illustrates a close-up view of an individual inflorescence of 'Balangflran'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2023 under natural light conditions in West Chicago, Ill.

The following descriptions and measurements describe approximately 4-month-old plants produced from cuttings from stock plants and grown under conditions comparable to those used in commercial practice. The plants were grown in West Chicago, Illinois in 3-gallon pots utilizing a soilless growth medium for approximately 9 weeks in an outdoor nursery in West Chicago, Ill. Plants were given three pinches prior to transplant. Eight weeks after cuttings were stuck, plants were sprayed with growth regulators B-NINE (daminozide[butanedioic acid mono (2,2-dimethylhydrazide)]) at 2,500 ppm and CYCOCEL (chlormequat (2-chloroethyl) trimethylammonium chloride) at 800 ppm. Prior to transplant plants were grown in a polycarbonate greenhouse in West Chicago, Ill. Greenhouse temperatures were maintained at approximately 75° F. to 80° F. (24° C. to 27° C.) during the day and approximately 65° F. to 70° F. (18° C. to 21° C.) during the night. Supplemental lighting was used during propagation stage. Measurements and numerical values represent averages of typical plants.

Botanical classification: *Angelonia angustifolia* 'Balangfiran'.

Parentage:

*Female parent*.—Proprietary *Angelonia angustifolia* breeding selection coded ANG-07360-01, not patented.

*Male parent*.—Proprietary *Angelonia angustifolia* breeding selection coded ANG-07321-01, not patented.

Propagation:

*Type cutting*.—Terminal stem.

*Time to initiate roots*.—Approximately 7 to 10 days.

*Time to produce a rooted cutting*.—Approximately 4 to 5 weeks.

*Root description*.—Fine, fibrous.

*Rooting habit*.—Freely branching.

Plant description:

*Commercial crop time*.—Approximately 6 weeks from a rooted cutting to finish in a 10 cm pot.

*Growth habit and general appearance*.—Vigorous, semi-upright.

*Size*.—Height from soil level to top of plant plane: Approximately 45.0 cm. Width: Approximately 50.0 cm.

*Branching habit*.—Freely branching, pinching improves basal branching. Quantity of main branches per plant: Approximately 7.

*Branch*.—Shape: Square in cross section. Strength: Moderately strong, somewhat brittle. Length: Approximately 31.0 cm. Diameter: Approximately 3.0 mm to 4.0 mm. Length of central internode: Approximately 1.3 cm. Texture: Moderately pubescent with minute hairs. Color of young and mature stems: 144A.

Foliage description:

*General description*.—Quantity of leaves per main branch: Approximately 30. Fragrance: None. Form: Simple. Arrangement: Opposite.

*Leaves*.—Aspect: Primarily perpendicular or obtuse angle to stem. Shape: Narrowly elliptic to narrowly ovate. Margin: Widely serrate. Apex: Acute. Base: Sessile. Venation pattern: Pinnate. Length of mature leaf: Approximately 5.2 cm. Width of mature leaf: Approximately 1.3 cm. Texture of upper surface: Glabrous. Texture of lower surface: Sparsely pubescent. Color of upper surface of young foliage: 137A with base of midvein of 146D, other venation indistinguishable. Color of lower surface of young foliage: 137B with midvein of 146D, other venation indistinguishable. Color of upper surface of mature foliage: NN137A with base of midvein of 146D, other venation indistinguishable. Color of lower surface of mature foliage: Closest to 137B with midvein of 146D, other venation indistinguishable.

Flowering description:

*Flowering habit*.—'Balangflran' is freely flowering under outdoor growing conditions with substantially continuous blooming from spring through autumn and year-round in greenhouse environment.

*Lastingness of individual flower on the plant*.—Approximately 7 to 10 days.

Inflorescence description:

*General description*.—Type: Terminal raceme. Quantity per plant: Approximately 75. Fragrance: Slight, sweet. Length: Approximately 19.5 cm. Width: Approximately 5.0 cm. Quantity of fully open flowers per inflorescence: Approximately 9.

Flower description:

*Type*.—Solitary, zygomorphic.

*Bud*.—Rate of opening: Generally takes 3 to 4 days for bud to progress from first color to fully open flower.

*Bud just before opening*.—Shape: Globular. Length: Approximately 6.0 mm. Diameter: Approximately 6.0 mm. Color of upper surface: 145A. Color of lower surface: 145C with 63C.

*Corolla*.—Shape: Bilabiate. Aspect: Facing outward. Length: Approximately 2.7 cm. Width: Approximately 2.6 cm. Depth: Approximately 9.0 mm.

*Petals*.—Quantity: 5 petals fused at base forming a throat and consisting of an upper lip with 2 petals and a lower lip with 3 petals, consisting of 2 lateral petals and one central petal. Shape: Obovate. Margin: Entire, slightly wavy. Apex: Obtuse.

*Upper lip*.—Length of petals from throat: Approximately 8.0 mm. Width of each petal: Approximately 1.4 cm. Texture of upper surface: Moderately glandular pubescent. Gland color: 150C and colorless, transparent. Texture of lower surface: Glabrous. Color of upper surface when fully open: 63A tinted with 83A near margin. Color of lower surface when fully open: 63A to 63B tinted with 83A.

*Lower lip, lateral petals*.—Length of petals from throat: Approximately 1.0 cm. Width of each petal: Approximately 1.1 cm. Texture of upper surface: Moderately glandular pubescent. Texture of lower surface: Densely glandular pubescent. Gland color: 150C and colorless, transparent. Color of upper surface when fully open: 63A with an overlay of 83A in a reticulate-like pattern. Color of lower surface when fully open: 63A to 63B faintly tinted with 83A.

*Lower lip, central petal*.—Length from the palate: Approximately 9.0 mm. Width: Approximately 1.0 cm. Texture of upper surface: Moderately glandular pubescent. Texture of lower surface: Densely glandular pubescent. Gland color: 150C and colorless, transparent. Color of upper surface when fully open: 63A with an overlay of 83A in a reticulate-like pattern. Color of lower surface when fully open: 63A to 63B faintly tinted with 83A.

*Throat*.—Length: Approximately 1.1 cm. Width: Approximately: 9.0 mm. Texture of inner surface: Sparsely glandular pubescent. Gland color: 150C, transparent. Texture of outer surface: Glabrous. Color of inner surface: 63A to 63B with spots of N79A. Color of outer surface: 83C with spots of N79A. Palate color: 83A with spots of N79A and occasionally with a patch a 146D near throat and/or a patch of NN155D at lower lip. Palate texture: Sparsely glandular pubescent. Gland color: 150C, transparent. Teeth color: 83A.

*Calyx*.—Shape: Star, cupped. Diameter: Approximately 7.0 mm.

*Sepals*.—Quantity per flower: 5, fused at base. Shape: Ovate. Apex: Acute. Length: Approximately 4.0 mm. Width: Approximately 2.0 mm. Texture of upper (inner) surface: Sparsely glandular pubescent. Texture of lower (outer) surface: Densely glandular pubescent. Gland color: Colorless, transparent. Color of upper (inner) surface: 146A. Color of lower (outer) surface: 146A with a heavy overlay of N186A.

*Pedicel*.—Strength: Strong, flexible. Aspect: Acute angle to stem. Length: Approximately 1.0 cm. Diameter: Approximately 1.0 mm. Texture: Densely glandular pubescent. Gland color: 150C and colorless, transparent. Color: 146B with a heavy overlay of 187A.

*Reproductive organs*.—Androecium: Stamen quantity: 4 per flower. Filament length: Approximately 3.0 mm. Filament texture: Sparsely glandular pubescent. Gland color: Colorless, transparent. Filament color: NN155D tinted with 63B. Anther shape: Bilobed. Anther length: Approximately 1.0 mm. Anther color: 83A. Pollen amount: Abundant. Pollen color: 155D. Gynoecium: Pistil quantity: 1 per flower. Pistil length: Approximately 4.0 mm. Stigma shape: Pointed. Stigma length: Less than 1.0 mm. Stigma color: NN155D. Style length: Approximately 3.0 mm. Style color: NN155D. Ovary diameter: Approximately 1.0 mm. Ovary texture: Sparsely glandular pubescent. Gland color: Colorless, transparent. Ovary color: 146B tinted with 83A.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangflran', substantially as herein illustrated and described.

* * * * *